(12) United States Patent
Kagaya

(10) Patent No.: US 8,008,635 B2
(45) Date of Patent: Aug. 30, 2011

(54) METHOD FOR SAMPLE PREPARATION

(75) Inventor: Yusuke Kagaya, Tokyo (JP)

(73) Assignee: Jeol, Ltd., Tokyo (JP)

( * ) Notice: Subject to any disclaimer, the term of this patent is extended or adjusted under 35 U.S.C. 154(b) by 110 days.

(21) Appl. No.: 12/258,663

(22) Filed: Oct. 27, 2008

(65) Prior Publication Data

US 2009/0126051 A1 May 14, 2009

(30) Foreign Application Priority Data

Nov. 8, 2007 (JP) ................................. 2007-290496

(51) Int. Cl.
*G08B 21/00* (2006.01)

(52) U.S. Cl. ................ 250/492.21; 250/309; 250/492.1; 250/492.3

(58) Field of Classification Search ................. 250/309, 250/492.1, 492.21, 492.3
See application file for complete search history.

(56) References Cited

U.S. PATENT DOCUMENTS

| | | | |
|---|---|---|---|
| 4,800,100 A * | 1/1989 | Herbots et al. ................. | 427/527 |
| RE33,193 E * | 4/1990 | Yamaguchi et al. ........... | 250/309 |
| 5,055,969 A * | 10/1991 | Putnam .......................... | 361/749 |
| 5,270,552 A | 12/1993 | Ohnishi et al. | |
| 6,303,932 B1 * | 10/2001 | Hamamura et al. ............ | 850/43 |
| 6,420,722 B2 * | 7/2002 | Moore et al. ................ | 250/559.27 |
| 6,538,254 B1 * | 3/2003 | Tomimatsu et al. ...... | 250/442.11 |
| 6,781,125 B2 * | 8/2004 | Tokuda et al. ................. | 850/1 |
| 6,828,566 B2 * | 12/2004 | Tomimatsu et al. ...... | 250/442.11 |
| 6,927,391 B2 * | 8/2005 | Tokuda et al. .................. | 850/10 |
| 7,071,475 B2 * | 7/2006 | Tomimatsu et al. ...... | 250/442.11 |
| 7,205,554 B2 * | 4/2007 | Tokuda et al. ............. | 250/492.1 |
| 7,205,560 B2 * | 4/2007 | Tokuda et al. ............. | 250/492.3 |
| 7,397,050 B2 * | 7/2008 | Tomimatsu et al. ..... | 250/492.21 |
| 7,470,918 B2 * | 12/2008 | Tokuda et al. ............. | 250/492.1 |
| 7,525,108 B2 * | 4/2009 | Tomimatsu et al. ..... | 250/492.21 |
| 7,550,750 B2 * | 6/2009 | Tokuda et al. ........... | 250/492.21 |
| 7,592,606 B2 * | 9/2009 | Ishiguro et al. .......... | 250/442.11 |
| 7,700,931 B2 * | 4/2010 | Shichi et al. ............. | 250/492.21 |
| 2009/0126051 A1 * | 5/2009 | Kagaya ........................... | 850/18 |

FOREIGN PATENT DOCUMENTS

| | | |
|---|---|---|
| JP | 2774884 | 4/1998 |
| JP | 2003-007246 | 1/2003 |
| JP | 2005-322419 | 11/2005 |

\* cited by examiner

*Primary Examiner* — David A Vanore

(74) *Attorney, Agent, or Firm* — The Webb Law Firm

(57) ABSTRACT

Method and system for preparing samples for use in electron microscopy. The method and system use a focused ion beam (FIB) instrument and a scanning electron microscope to improve the time efficiency of the FIB instrument. The FIB instrument incorporates machining means for preparing thin-film samples by ion beam irradiation. The scanning electron microscope incorporates a gas supply means and a manipulator equipped with a probe. The gas supply means ejects gas at the sample after it has been shifted from the FIB instrument together with a sample holder. The sample is irradiated with an electron beam while the gas is injected at the sample from the gas supply means under the condition where the probe is contacted with the sample. Thus, the sample is bonded to the probe.

2 Claims, 2 Drawing Sheets

METHOD FOR SAMPLE PREPARATION

BACKGROUND OF THE INVENTION

1. Field of the Invention

The present invention relates to a method and system for sample preparation and, more particularly, to a method and system for preparing thin-film samples for transmission electron microscopy and sections of samples to be observed by scanning electron microscopy by making use of a focused ion beam (FIB) instrument and a scanning electron microscope (SEM).

2. Description of Related Art

One conventional method of preparing samples is disclosed, for example, in Japanese Patent No. 2,774,884 (paragraphs 0010 to 0018; FIGS. 1-6). In this method, the surface of the base plate of a sample is machined by a focused ion beam (FIB) from at least two angles to the surface of the base plate to isolate a tiny portion of the sample. At this time, the tip of a probe is connected with the isolated tiny sample portion. The sample portion can be conveyed into any arbitrary position by moving the probe.

Another conventional system is disclosed, for example, in JP-A-2003-7246 (paragraphs 0011 to 0030; FIGS. 3 and 4), and uses a transmission electron microscope equipped with two preliminary chambers. Each chamber has a focused ion beam instrument. When the first preliminary chamber is used for sample preparation, a sample from the second preliminary chamber is observed. When the second preliminary chamber is used for sample preparation, a sample from the first preliminary chamber is observed.

A further conventional charged-particle beam system is disclosed, for example, in JP-A-2005-322419 (paragraphs 0015 to 0017; FIG. 2) and uses a common moving device on which both a sample supply portion and a probe are carried when the sample is bonded to the probe.

(Sample Preparation for TEM)

In the technique of the above-cited Japanese Patent No. 2,774,884, sample preparation using a focused ion beam (FIB) instrument and moving of the prepared sample are carried out within one apparatus. This produces the problem that the time efficiency is low. Alternatively, a sample prepared by an FIB instrument has been moved to an optical microscope equipped with a manipulator and conveyed. In this equipment, the magnification of the optical microscope is low. Furthermore, it is difficult to convey the sample by the manipulator (glass probe). Hence, the sample has been conveyed at a low rate of success.

(Observations of Cross Sections for SEM)

A cross section of a sample has been observed by forming a hole by the machining function of an FIB instrument to thereby expose the cross section and then the cross section has been observed by making use of the SEM stage-tilting mechanism. There is the problem that the cross section to be observed is made invisible and, thus, made unobservable by sample tilting unless the hole is increased in area.

SUMMARY OF THE INVENTION

It is an object of the present invention to provide a method and system permitting samples to be prepared in such a way that the time efficiency of a focused ion beam (FIB) instrument is improved and the samples are conveyed at improved rates of success and that sample cross sections can be observed by SEM under improved conditions although both the FIB instrument and a scanning electron microscope are utilized.

A first embodiment of the present invention provides a method for sample preparation. This method starts with preparing a scanning electron microscope having gas supply means for supplying gas to surround a sample and a manipulator equipped with a probe. A thin-film sample is prepared using the machining function of a focused ion beam (FIB) instrument. The prepared sample is shifted to the scanning electron microscope together with a sample holder. The sample is irradiated with an electron beam while injecting the gas at the sample from the gas supply means under the condition where the probe is contacted with the sample, whereby the sample is bonded to the probe.

A second embodiment of the present invention provides a sample preparation system consisting of a focused ion beam (FIB) instrument and a scanning electron microscope. The FIB instrument has machining means for preparing a thin-film sample by ion beam irradiation. The scanning electron microscope has gas supply means and a manipulator equipped with a probe. When the sample has been shifted from the (FIB) instrument to the scanning electron microscope together with a sample holder, the gas supply means injects gas at the sample while the probe is contacted with the sample. At the same time, the sample is irradiated with an electron beam. As a result, the sample is bonded to the probe.

According to the first embodiment of the present invention, the sample preparation step and the sample shifting step can be carried out independently. Therefore, when the sample is being taken out of the FIB instrument, the operation of the FIB instrument is not affected. Another sample can be prepared simultaneously. Samples are conveyed by the SEM instead of an optical microscope. Consequently, each sample can be bonded to the tip of the probe controlled by the manipulator. This method is free of the problem of low magnifications of an optical microscope. Furthermore, the method is free of the problem that it is difficult to convey a sample with a manipulator (glass probe). A cross section can be observed by the SEM after the sample has been taken out. As a result, a clearer cross-sectional image can be observed by the SEM easily.

According to the second embodiment of the present invention, the sample preparation step and the sample shifting step can be carried out independently, in the same way as in the first embodiment. Therefore, when the sample is being taken out, the operation of the FIB instrument is not affected. Another sample can be prepared simultaneously. Samples are conveyed by the SEM instead of an optical microscope. Consequently, each sample can be bonded to the probe at the tip of the manipulator. This sample preparation system is free of the problem of low magnifications with an optical microscope. Furthermore, the sample preparation system is free of the problem that it is difficult to convey a sample with a manipulator (glass probe). In consequence, a cross section can be observed by the SEM after the sample has been taken out. As a result, a clearer cross-sectional image can be observed by the SEM easily.

Other objects and features of the invention will appear in the course of the description thereof, which follows.

DESCRIPTION OF THE PREFERRED EMBODIMENTS

The preferred embodiments of the present invention are hereinafter described in detail with reference to the drawings.

Figure 1:
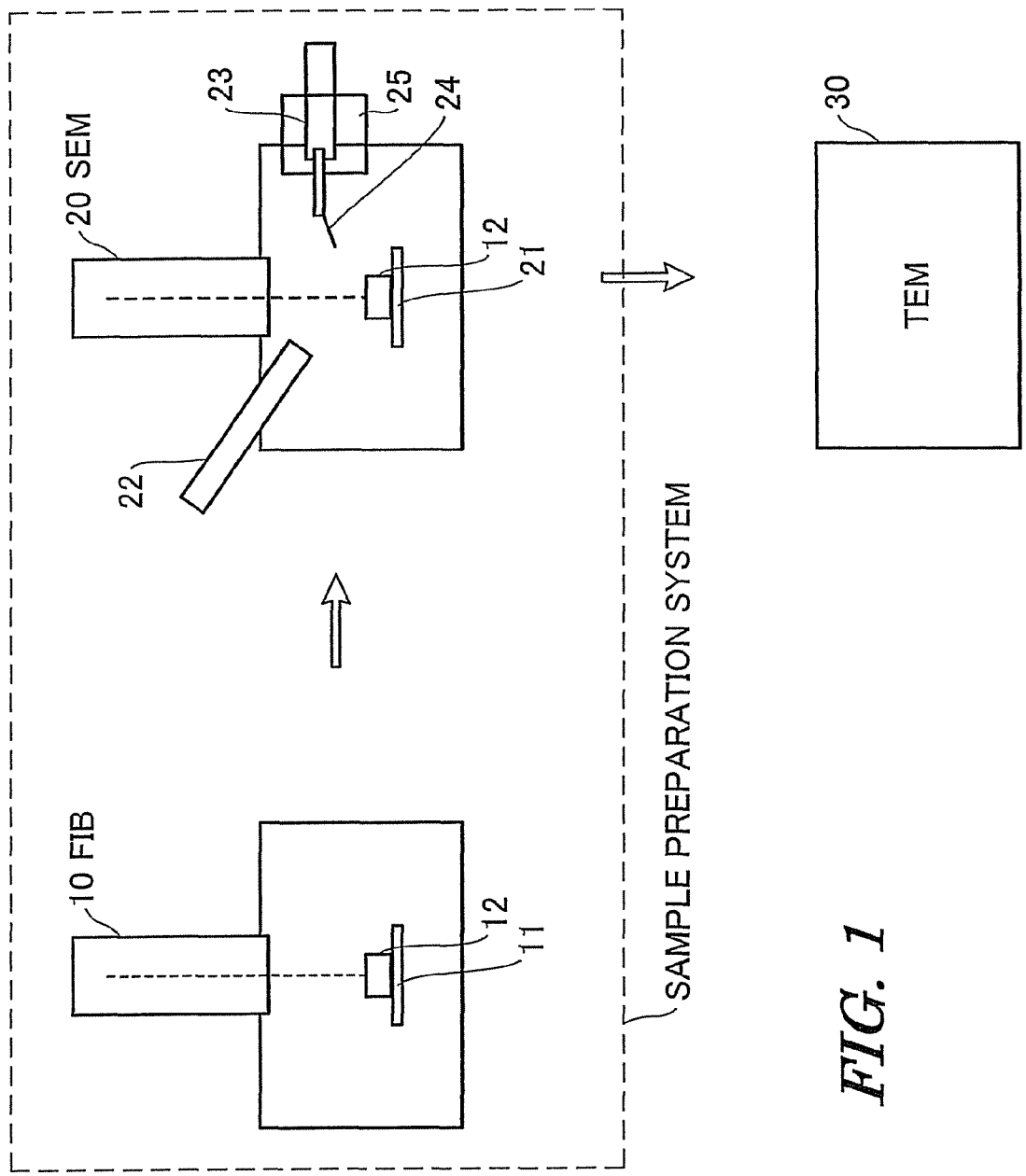
FIG. 1 illustrates a system configuration depicting one embodiment of the present invention.

In FIG. 1, a sample preparation system, according to one embodiment of the present invention, has a focused ion beam (FIB) instrument 10, and a scanning electron microscope (SEM) 20. The FIB instrument 10 includes a sample stage 11 on which a sample holder 12 is placed. A sample (not shown) is attached on the sample holder 12.

The sample holder 12 is shifted into the scanning electron microscope 20 from the FIB instrument 10. A sample stage 21 is mounted within the scanning electron microscope 20. The sample holder 12 shifted from the FIB instrument 10 is placed on the sample stage 21. The sample (not shown) is attached on the sample holder 12.

The scanning electron microscope further includes a sample deposition device 22 acting as a gas supply means for injecting gas, a manipulator 23 for taking out the sample, a probe 24 attached to the tip of the manipulator 23, and an airlock chamber 25. The probe 24 can be moved into a desired position by the manipulator 23. The airlock chamber 25 permits the probe to be exchanged without exposing the inside of the SEM sample chamber to the atmospheric pressure.

A transmission electron microscope (TEM) 30 is used for sample observation.

The operation of the sample preparation system constructed as described so far by referring to FIG. 1 is next described. The operation includes a bonding step illustrated in FIG. 2.

(I) Step for Preparing a TEM Sample
(Sample Preparation Step)

Step 1: The sample holder 12 is set on the sample stage 11 of the FIB instrument 10. It is assumed that the sample (not shown) has been already attached on the sample holder 12.

Step 2: Thin TEM samples are prepared at plural locations on the sample, using the machining function of the FIB instrument 10. Because the ion beam has high energy, the portions of the sample irradiated with the ion beam are etched away. At this time, the thin-film samples are completely isolated from the matrix of the bulk sample or narrowly held on it.

(Step for Taking Out Thin-Film Samples)

Step 3: The thin-film samples prepared in step 2 are shifted onto the sample stage 21 of the scanning electron microscope 20 together with the sample holder 12. This operation may be done manually by the human operator or automatically using an automatic transport mechanism.

Step 4: At this time, the scanning electron microscope 20 is operated, for example, to obtain secondary electron images of the thin-film samples. The secondary electron images are displayed on a display device (not shown) attached to the scanning electron microscope 20. The operator manipulates the knob (not shown) of the manipulator 23 to bring the tip of the probe 24 controlled by the manipulator 23 into contact with the thin-film samples prepared in step 2 while observing the displayed secondary electron images of the thin-film samples.

Step 5: The thin-film samples are irradiated with an electron beam while supplying gas by the deposition device 22, to bond the thin-film samples, which were contacted with the probe 24 at step 4, to the probe 24 at the end of the manipulator.

Figure 2:
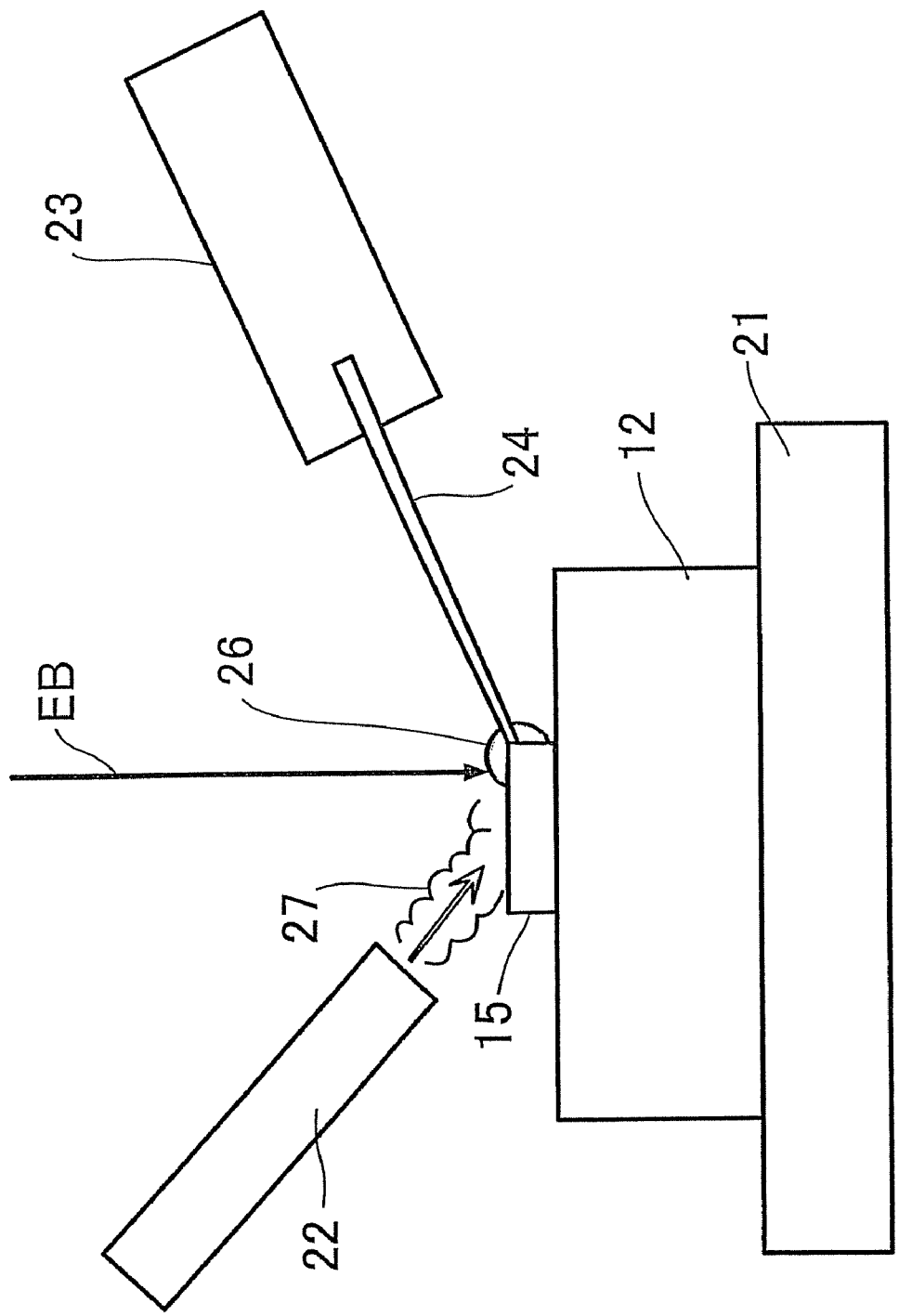
FIG. 2 illustrates a manner in which a thin-film sample is bonded according to the present invention.

FIG. 2 illustrates the manner in which the thin-film samples are bonded. In both FIGS. 1 and 2, like components are indicated by like reference numerals. The probe 24 attached to the manipulator 23 is brought into contact with a sample 15. At the same time, desired gas 27 is injected at the sample 15 from the deposition device 22. Under this condition, the sample 15 is irradiated with an electron beam EB. A deposition film is formed between the probe 24 and the sample 15 by the deposition effect of the gas, thus bonding the sample 15 to the probe 24 at 26.

Step 6: Pieces of the sample are taken from the matrix by utilizing the drive mechanism of the manipulator 23.

Step 7: The sample pieces bonded to the tip of the probe 24 are taken out into the atmosphere by employing the airlock chamber 25 (not shown in FIG. 2).

Step 8: Where the sample 15 is etched at plural locations, a new probe is inserted into the manipulator 23, and steps S4-S6 are repeatedly performed.

The sample pieces prepared in this way are attached to the tip of the probe 24. The sample pieces are set on the dedicated sample holder (not shown in FIG. 2) and mounted to the transmission electron microscope 30 (FIG. 1). In particular, the sample holder is mounted to the sample stage of the TEM 30. Under this condition, the electron beam is directed at the sample pieces. A TEM image of the sample pieces is observed, for example, on a fluorescent screen or shot by a television camera and then observed on the display device of the TEM. If the sample holder is designed to be rotatable, the sample pieces can be rotated through a slight angle to permit cross-sectional shapes of the sample pieces to be seen best.

(II) Step for Observing Cross Sections in SEM
(Sample Preparation Step)

Step 1: A sample is set on the sample stage 11 of the focused ion beam instrument 10.

Step 2: Bulk samples having arbitrary shapes are prepared at plural locations on the sample using the machining function of the focused ion beam instrument 10. At this time, the sample is completely isolated from the matrix or narrowly held on it.

(Step for Taking Out Bulk Samples)

Step 3: The bulk samples prepared in step 2 are shifted onto the sample stage 21 of the scanning electron microscope 20 together with the sample holder 12. This operation may be done manually by an operator or automatically using the automatic transfer mechanism.

Step 4: The operator manipulates the control portion (not shown) to bring the probe 24 mounted at the tip of the manipulator 23 into contact with the thin-film samples prepared in step 2 while observing, for example, secondary electron images on the SEM 20.

Step 5: The thin-film samples are irradiated with an electron beam EB while supplying gas from the deposition device 22. The thin-film samples 15 contacted with the probe 24 in step 4 are bonded to the probe 24 at the tip of the manipulator 23 by the deposition effect in the manner already described in connection with FIG. 2. That is, desired gas 27 is injected at the samples 15 from the deposition device 22. Under this condition, the samples 15 are irradiated with the electron beam EB. A deposition film is formed between the probe 24 and the samples 15 by the deposition effect of the gas. The samples 15 are bonded to the probe 24 at 26.

Step 6: Sample pieces are extracted from the matrix by utilizing the drive mechanism of the manipulator 23.

(Sample Observation Step 1)

Step 7: The sample pieces are tilted by a tilt drive mechanism whose axis of rotation is coincident with the direction in which the manipulator 23 is inserted.

Step 8: SEM observations are made while the sample pieces are bonded to the probe 24.

(Sample Observation Step 2)

Step 7: The sample pieces bonded to the tip of the probe 24 are taken out into the atmosphere by utilizing the airlock chamber 25.

Step 8: The probe 24 taken out is set on a dedicated holder that can be mounted to a bulk stage and again inserted into the SEM sample chamber. Then, the sample pieces are observed.

As described so far, according to the present invention, the step of preparing samples and the step of shifting the samples can be carried out independently. When the samples are being taken out, the operation of the FIB instrument 10 is not affected. Other samples can be prepared simultaneously. Furthermore, the samples can be bonded to the probe 24 that is controlled by the manipulator 23 by shifting the samples by the SEM 20 rather than by an optical microscope. In consequence, low magnification problems with optical microscopes do not take place. In addition, the problem that it is difficult to convey the samples by a manipulator (glass probe) does not take place. Moreover, cross sections can be observed with the SEM 20 after the samples are taken out. Hence, clearer cross-sectional images can be observed with the SEM 20 simply.

In the above embodiments, the focused ion beam instrument 10 has only the ion beam-emitting function. Instead, an instrument having both an electron beam-emitting function and a secondary electron imaging function may also be used. The present invention yields especially great advantages in cases where the focused ion beam instrument is equipped with no manipulator. If a manipulator is mounted, a machining operation using an ion beam and a device for taking out samples can be done concurrently.

Having thus described my invention with the detail and particularity required by the Patent Laws, what is desired protected by Letters Patent is set forth in the following claims.

The invention claimed is:

1. A method for sample preparation, comprising the steps of:
   providing a sample preparation system having a focused ion beam instrument for sample machining and an independent and spaced scanning electron microscope;
   preparing said scanning electron microscope having gas supply means for supplying gas to surround a sample and having a manipulator equipped with a probe;
   preparing a thin-film sample on a sample holder using a machining function of said focused ion beam instrument;
   shifting the prepared thin-film sample to said scanning electron microscope together with a sample holder; and
   irradiating the thin-film sample with an electron beam of said electron microscope while injecting the gas at the thin-film sample from the gas supply means under the condition where the probe is contacted with the sample, whereby the thin-film sample is bonded to the probe.

2. A method for sample preparation, comprising the steps of:
   providing a sample preparation system having a focused ion beam instrument for sample machining and an independent and spaced scanning electron microscope;
   preparing said scanning electron microscope having gas supply means for supplying gas to surround a sample and having a manipulator equipped with a probe with associated air-lock chamber;
   preparing a thin-film sample on a sample holder using a machining function of said focused ion beam instrument;
   shifting the prepared thin-film sample to said scanning electron microscope together with a sample holder; and
   irradiating the thin-film sample with an electron beam of said electron microscope while injecting the gas at the thin-film sample from the gas supply means under the condition where the probe is contacted with the sample, whereby the thin-film sample is bonded to the probe, and removing the thin-film sample via the air-lock chamber.

* * * * *